(12) United States Patent
Benoist et al.

(10) Patent No.: US 7,662,375 B2
(45) Date of Patent: Feb. 16, 2010

(54) USE OF GLUCOSE-6-PHOSPHATE ISOMERASE AND ANTIBODIES THERETO FOR THE DIAGNOSIS AND THERAPY OF ARTHRITIS, AND TEST OF ANTI-ARTHRITIC COMPOUNDS

(75) Inventors: Christophe Benoist, Strasbourg (FR); Isao Matsumoto, Strasbourg (FR); Anne-Sophie Korganow, Strasbourg (FR); Diane Mathis, Strasbourg (FR); Mariana Maccioni, Illkirch (FR); Hong Ji, Illkirch (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 11/360,515

(22) Filed: Feb. 24, 2006

(65) Prior Publication Data

US 2006/0143723 A1    Jun. 29, 2006

Related U.S. Application Data

(62) Division of application No. 09/959,230, filed on Oct. 22, 2001, now Pat. No. 7,033,745.

(51) Int. Cl.
*A61K 39/395* (2006.01)
*A61K 39/00* (2006.01)
*G01N 33/00* (2006.01)
*C12P 21/00* (2006.01)

(52) U.S. Cl. .............. 424/130.1; 424/139.1; 424/158.1; 800/3; 800/4; 800/5; 800/6

(58) Field of Classification Search ........................ None
See application file for complete search history.

(56) References Cited

OTHER PUBLICATIONS

Colman et al. 'Effects of amino acid sequence changes on antibody-antigen interactions.' Research in Immunology 145(1):33-36, 1994.*
Abaza et al. 'Effects of amino acid substitutions outside an antigenic site on protein binding to monoclonal antibodies of predetermined specificity obtained by peptide immunization: demonstration with region 94-100 (antigenic site 3) of myoglobin.' J. Prot. Chem. 11(5):433-444, 1992.*
Lederman et al. 'A single amino acid substitution in a common African allele of the CD4 molecule ablates binding of the monoclonal antibody, OKT4.' Molec. Immunol. 28:1171-1181, 1991.*
McDevitt et al. A new model for rheumatoid arthritis? Arthritis Res. 2:85-89, 2000.*
Korganow et al. 'From systemic T cell self-reactivity to organ-specific autoimmune disease via immunoglobulins.' Immunity 10:451-461, 1999.*
Maccioni et al. 'Arthritogenic monoclonal antibodies from K/BxN mice.' J. Exp. Med. 195(8):1071-1077, 2002.*
Schubert et al. 'Immunization with glucose-6-phosphate isomerase induces T cell-dependent peripheral polyarthritis in genetically unaltered mice.' J. Immunol. 172:4503-4509, 2004.*
Conrad, U. et al., "Immunochemical Differentiation of Glucose Phosphate Isomerase (GPI) Allozymes of the Mouse," Biochem. Genet., vol. 25, Nos. 9-10, pp. 739-754, 1987.
Database WPI, "Inducing Immune Response Against a Microorganism, Useful Particularly for Treating or Preventing Malaria, by Administering an Inositolglycan Domain of Glycosylphosphatidylinositol," & WO 00\15254, Hall Inst. Medical Res. Walter & Eliza, Mar. 23, 2000, Abstract.
Feldmann M. et al., "Rheumatoid Arthritis," Cell, vol. 85, No. 3, pp. 307-310, May 3, 1996.
Kouskoff V. et al., "Organ-Specific Disease Provoked by Systemic Autoimmunity," Cell, vol. 87, No. 5, pp. 811-822, Nov. 29, 1996.
Matsumoto I et al., "Arthritis Provoked By Linked T and B Cell Recongnition of a Glycolytic Enzyme," Science, vol. 286, No. 5445, pp. 1732-1735, Nov. 26, 1999.
Walker, James, I.H. et al., "Structure and Organization of the Human Glucose Phosphate Isomerase Gene (GPI)," Genomics, vol. 29, No. 1, pp. 261-265, 1995.

* cited by examiner

*Primary Examiner*—Maher M Haddad
*Assistant Examiner*—Nora M Rooney
(74) *Attorney, Agent, or Firm*—Foley & Lardner LLP

(57) ABSTRACT

The present invention relates to the use of antibodies against glucose-6-phosphate isomerase (GPI) and like protein for diagnosis of arthritis and the use of said protein for treatment of arthritis. It is also aimed at a process for isolating monoclonal antibodies capable of transferring arthritis and antibodies thereof, as well as a method for determining the antiarthritis potential of a composition.

1 Claim, 9 Drawing Sheets

Figure 1A:

FIGURE 2

```
  1 MAALTRNPQFQKLLEWHRANSANLKLRELFEADPERFNNESLNLNTNHGHILVDYSKNLV
 61 NKEVMQMLVELAKSRGVEAARDNMFSGSKINYTEDRAVLHVALRNRSNTPIKVDGKDVMP
121 EVNRVLDKMKSFCQRVRSGDWKGYTGKSITDIINIGIGGSDLGPLMVTEALKPYSKGGPR
181 VWFVSNIDGTHIAKTLASLSPETSLFIIASKTFTTQETITNAETAKEWFLEAAKDPSAVA
241 KHFVALSTNTAKVKEFGIDPQNMEEFWDWVGGRYSLWSAIGLSIALHVGFDHFEQLLSGA
301 HWMDQHFLKTPLEKNAPVLLALLGIWYINCYGCETHALLPYDQYMHRFAAYFQQGDMESN
361 GKYITKSGARVDHQTGPIVWGEPGTNGQHAFYQLIHQGTKMIPCDFLIPVQTQHPIRKGL
421 HHKILLANFLAQTEALMKGKLPEEARKELQAAGKSPEDLEKLLPHKVFEGNRPTNSIVFT
481 KLTPFILGALIAMYEHKIFVQGIMWDINSFDQWGVELGKQLAKKIEPELEGSSAVTSHDS
541 STNGLISFIKQQRDTKLE
```

FIGURE 4

SEQUENCE LISTING

```
<160> NUMBER OF SEQ ID NOS: 1

<210> SEQ ID NO 1
<211> LENGTH: 558
<212> TYPE: PRT
<213> ORGANISM: Mus musculus
<220> FEATURE:
<223> OTHER INFORMATION: Glucose-6-phosphate isomerase

<400> SEQUENCE: 1

Met Ala Ala Leu Thr Arg Asn Pro Gln Phe Gln Lys Leu Leu Glu Trp
 1               5                  10                  15

His Arg Ala Asn Ser Ala Asn Leu Lys Leu Arg Glu Leu Phe Glu Ala
                20                  25                  30

Asp Pro Glu Arg Phe Asn Asn Phe Ser Leu Asn Leu Asn Thr Asn His
            35                  40                  45

Gly His Ile Leu Val Asp Tyr Ser Lys Asn Leu Val Asn Lys Glu Val
        50                  55                  60

Met Gln Met Leu Val Glu Leu Ala Lys Ser Arg Gly Val Glu Ala Ala
 65                  70                  75                  80

Arg Asp Asn Met Phe Ser Gly Ser Lys Ile Asn Tyr Thr Glu Asp Arg
                85                  90                  95

Ala Val Leu His Val Ala Leu Arg Asn Arg Ser Asn Thr Pro Ile Lys
            100                 105                 110

Val Asp Gly Lys Asp Val Met Pro Glu Val Asn Arg Val Leu Asp Lys
        115                 120                 125

Met Lys Ser Phe Cys Gln Arg Val Arg Ser Gly Asp Trp Lys Gly Tyr
    130                 135                 140

Thr Gly Lys Ser Ile Thr Asp Ile Ile Asn Ile Gly Ile Gly Gly Ser
145                 150                 155                 160

Asp Leu Gly Pro Leu Met Val Thr Glu Ala Leu Lys Pro Tyr Ser Lys
                165                 170                 175

Gly Gly Pro Arg Val Trp Phe Val Ser Asn Ile Asp Gly Thr His Ile
```

-continued

```
            180                 185                 190
Ala Lys Thr Leu Ala Ser Leu Ser Pro Glu Thr Ser Leu Phe Ile Ile
        195                 200                 205
Ala Ser Lys Thr Phe Thr Thr Gln Glu Thr Ile Thr Asn Ala Glu Thr
        210                 215                 220
Ala Lys Glu Trp Phe Leu Glu Ala Ala Lys Asp Pro Ser Ala Val Ala
225                 230                 235                 240
Lys His Phe Val Ala Leu Ser Thr Asn Thr Ala Lys Val Lys Glu Phe
                245                 250                 255
Gly Ile Asp Pro Gln Asn Met Phe Glu Phe Trp Asp Trp Val Gly Gly
                260                 265                 270
Arg Tyr Ser Leu Trp Ser Ala Ile Gly Leu Ser Ile Ala Leu His Val
                275                 280                 285
Gly Phe Asp His Phe Glu Gln Leu Leu Ser Gly Ala His Trp Met Asp
                290                 295                 300
Gln His Phe Leu Lys Thr Pro Leu Glu Lys Asn Ala Pro Val Leu Leu
305                 310                 315                 320
Ala Leu Leu Gly Ile Trp Tyr Ile Asn Cys Tyr Gly Cys Glu Thr His
                325                 330                 335
Ala Leu Leu Pro Tyr Asp Gln Tyr Met His Arg Phe Ala Ala Tyr Phe
                340                 345                 350
Gln Gln Gly Asp Met Glu Ser Asn Gly Lys Tyr Ile Thr Lys Ser Gly
                355                 360                 365
Ala Arg Val Asp His Gln Thr Gly Pro Ile Val Trp Gly Glu Pro Gly
                370                 375                 380
Thr Asn Gly Gln His Ala Phe Tyr Gln Leu Ile His Gln Gly Thr Lys
385                 390                 395                 400
Met Ile Pro Cys Asp Phe Leu Ile Pro Val Gln Thr Gln His Pro Ile
                405                 410                 415
Arg Lys Gly Leu His His Lys Ile Leu Leu Ala Asn Phe Leu Ala Gln
                420                 425                 430
Thr Glu Ala Leu Met Lys Gly Lys Leu Pro Glu Glu Ala Arg Lys Glu
                435                 440                 445
Leu Gln Ala Ala Gly Lys Ser Pro Glu Asp Leu Glu Lys Leu Leu Pro
450                 455                 460
His Lys Val Phe Glu Gly Asn Arg Pro Thr Asn Ser Ile Val Phe Thr
465                 470                 475                 480
Lys Leu Thr Pro Phe Ile Leu Gly Ala Leu Ile Ala Met Tyr Glu His
                485                 490                 495
Lys Ile Phe Val Gln Gly Ile Met Trp Asp Ile Asn Ser Phe Asp Gln
                500                 505                 510
Trp Gly Val Glu Leu Gly Lys Gln Leu Ala Lys Lys Ile Glu Pro Glu
        515                 520                 525
Leu Glu Gly Ser Ser Ala Val Thr Ser His Asp Ser Ser Thr Asn Gly
        530                 535                 540
Leu Ile Ser Phe Ile Lys Gln Gln Arg Asp Thr Lys Leu Glu
545                 550                 555
```

USE OF GLUCOSE-6-PHOSPHATE ISOMERASE AND ANTIBODIES THERETO FOR THE DIAGNOSIS AND THERAPY OF ARTHRITIS, AND TEST OF ANTI-ARTHRITIC COMPOUNDS

The application is a Divisional of application Ser. No. 09/959,230 filed Oct. 22, 2001, issued as U.S. Pat. No. 7,033,745.

The present invention relates to the use of antibodies against glucose-6-phosphate isomerase and like protein for diagnosis of arthritis and the use of said protein for treatment of arthritis.

Rheumatoid arthritis (RA) is a frequent and incapacitating autoimmune disorder (Feldmann et al. 1996). It is a chronic, progressive joint disease, characterized by leukocyte invasion of the synovial lining and hyperplasia of the resident synoviocytes. The ensuing overproduction of cytokines and other soluble mediators results in cartilage destruction, bone erosion and anarchic remodelling of joint structures. The etiology and pathogenesis of RA remain controversial. It is not known whether disease is initiated by an unrestrained inflammatory reaction to a microbial antigen (Ag), an inappropriate autoimmune response to a self-constituent, or both. An important role for T cells (Panayi et al., 1992), B cells (Zvaifler, 1973), and other leukocytes such as dendritic cells, macrophages and neutrophils (Thomas and Lipsky, 1996) has been argued, and disputed. The lack of a consensus largely reflects two factors. RA is a heterogeneous syndrome, different patients exhibiting widely variant ages of onset, disease courses, genetic profiles and responses to therapeutic intervention. In addition, there has been a dearth of small animal models of RA, particularly those spontaneously succumbing to disease.

Recently, we generated a new transgenic mouse model of arthritis that spontaneously develops a disease with many of the characteristics of rheumatoid arthritis in humans ((Kouskoff et al., 1996), U.S. Pat. No. 5,675,060). All KRN T cell receptor (TCR) transgenic (tg) mice on the C57Bl/6xNOD genetic background (hereafter abbreviated as K/BxN mice) develop a joint disorder, starting at three to four weeks of age, and rapidly evolving until the animal's mobility is severely compromised; as in patients, the disease is chronic, progressive, symmetrical and has a proximal to distal gradient of severity. The murine disease exhibits all of the major histological features of the human one: leukocyte invasion, synovitis, pannus formation, cartilage and bone destruction, anarchic remodelling. The mouse model, like patients, shows several immunological abnormalities, including B cell hyperactivity manifest as an increase in B cell numbers, hypergammaglobulinemia and autoantibody production.

The disease in K/BxN mice is initiated by cross-reactive recognition of NOD-derived $A^{g7}$ molecules of the Major Histocompatibility Complex by the KRN TCR. Thus, in K/BxN animals, a situation of systemic autoreactivity is generated, raising the issue of how joint-specific autoimmune disease develops in the presence of systemic autoreactivity. We have reported earlier that T lymphocytes are required for arthritis development, as their blockade of T lymphocytes prevents disease, although they appear dispensable at the later stages of disease. B lymphocytes are also critical (Kouskoff et al., 1996).

In the present invention, we find that B cells are required for spontaneous arthritis because they produce pathogenic immunoglobulin directed against a target we identify as glucose-6-phosphate isomerase (EC 5.3.1.9). We show that recombinant glucose-6-phosphate isomerase can be used in diagnostic tests of murine arthritis, and to adsorb pathogenic immunoglobulins.

Autoantibodies have been previously reported in situations of induced arthritis in animal models, when disease is induced by immunization with cartilage components, such as type II collagen. Antibodies against ubiquitously expressed proteins have not been previously found to be arthritogenic.

Autoantibodies are also found in serum from RA patients, and have some diagnostic value. Rheumatoid factor (RF; Ab against the Fc portion of IgG) has been considered a hallmark of this disease; however, it is absent from about 30% of RA patients and is present in individuals with other autoimmune diseases (Mannik, 1992; Rudolphi et al., 1997) or in situation of chronic immune stimulation. Abs against cartilage or epidermal components have also been detected in RA patients, directed against Type II collagen (cII) or filaggrin, for example, but, again, these generally show limited correlation with disease parameters (Rudolphi et al., 1997; Claque and Moore, 1984; Sebbag et al., 1995).

The present invention deals with antibodies against glucose-6-phosphate isomerase (GPI) and glucose-6-phosphate isomerase like proteins (GPI like).

Said antibodies may be polyclonal or monoclonal and the technologies used for their preparation are known by the man skilled in the art.

GPI like proteins are proteins found in the serum, antibodies against whom have arthritogenic potential. Said GPI like are generally expressed in many tissues but always released in the serum, but are unable to induce complete immunological tolerance, and are thus the target of autoreactive T lymphocytes and/or autoantibodies.

GPI like proteins may also be proteins or polypeptides which contain at least one epitope able to interfere with anti-GPI or anti-GPI like antibodies, especially autoantibodies. Such proteins or polypeptides may be synthetic or recombinant and may encompass sequences of other proteins, especially said proteins or polypeptides when used for therapeutic application are not able to induce any pathology.

Examples of the present invention give the man skilled in the art detailed indications on how to identify GPI like proteins. In this regard, the present invention provides a test to isolate GPI like proteins and determine their arthritogenic property. One possible routine procedure is:
  obtaining serum from arthritic mammals, such as the K/BxN transgenic mice,
  preparing different IgG fractions of said serum and testing them for their ability to induce arthritis and eventually preparing subfractions based on these fractions,
  preparing an affinity chromatography column with IgG of said fractions,
  isolating and purifying GPI like proteins from proteins extracts from organs of the same mammal by means of said column.

These isolated proteins, defined as GPI like proteins, can be further characterized by means of standard techniques such as sequencing. Technical details on the experiments performed that led to the identification of GPI are described in Matsumoto I. et al (1999) and Korganow A S. et al (1999), incorporated herein by reference.

Therefore, another aspect of the invention is directed to a process for isolating GPI like proteins comprising the steps consisting of:
  preparing different IgG fractions or subfractions from serum of arthritic mammals, preferably from the K/BxN transgenic mice, isolating GPI like proteins by affinity chromatography with IgG of said fractions as matrix.

Said GPI like proteins are essentially enzymes, for example an enzyme involved in the hexose metabolism pathway, preferably GPI analogs.

The invention also concerns the use of the GPI or GPI like proteins and antibodies thereto obtainable by the process as depicted above for the treatment and diagnosis of arthritis.

Antibodies according the invention are different from the known arthritogenic antibodies described in the prior art which are directed against cartilage components such a Type II collagen. The antibodies of the present invention are mainly directed against proteins, which are expressed in many non-articular tissues, but released in the serum.

Another embodiment of the present invention deals with a process for diagnosis of arthritis which comprises detection of autoantibodies against GPI or GPI like proteins in the sample of plasma or serum of a patient.

The method of testing for the presence or amount of antibodies against GPI or GPI like proteins present in a sample comprises binding said proteins to the antibodies in the sample and detecting antibodies bound to said proteins.

The processes for detection of antibodies in the plasma or serum are well known in the art, for example ELISA or RIA tests may be used. It is possible to use a substrate coated with GPI or GPI like proteins, for example an assay plate, and then detect the presence of antibodies fixed on said GPI with appropriate labeled antibodies. Among the labels, those who are preferred are radioactive isotopes, compounds containing an isotope, enzymes, in particular enzymes susceptible to react with chromogenes, fluorigenes or luminescents (for example a peroxydase or an alcaline phosphatase), chromophores, chromogene compounds, fluorigenes ou luminescents, base analogues, and ligands such as biotin.

According to the present invention, GPI or GPI like proteins may be the natural protein itself, recombinant protein, synthetic protein or only the recombinant epitope of said proteins which are also encompassed by the terminology GPI like. So, the present invention also deals with a kit for carrying out the diagnosis of antibodies against GPI or GPI like proteins comprising a diagnostic agent consisting of a protein which is GPI or GPI like or an epitope thereof capable of interacting with an autoantibody of the plasma or the serum and a second antibody able to bind to said autoantibody, said second antibody being labelled for detection.

In another embodiment, the present invention concerns the use of GPI or GPI like proteins including portion of said GPI like which are able to interact with autoantibodies to inhibit or remove said autoantibodies for treatment or prevention of arthritis.

The invention also deals with the expression of GPI or GPI like proteins in vivo through the use of a vector comprising elements sufficient for expressing in vivo said GPI or GPI like proteins. Said vector may be from viral origin, may be plasmid or may be purely synthetic or naked DNA as described in VICAL technology. Expression of said proteins will provide GPI like proteins to adsorb arthritogenic antibodies (see the examples of said specification).

The efficacy of potential anti-arthritic compositions can be evaluated by determining the effect of the compositions on arthritis induced in normal mice by injection of serum from K/BxN mice, or of immunoglobulins derived therefrom, or of anti-GPI or anti-GPI like antibodies. Compositions thus evaluated include, but are not limited to, chemical compounds, biologicals such as antibodies, polypeptides, anti-inflammatory agents, hormones, tolerogens, which inhibit the binding of anti-GPI or anti-GPI like antibodies to their targets or the pathological consequences of this binding.

This can be done by: i) administering a known dose of arthritogenic serum or immunoglobulins to a first non-arthritic mouse, said mouse also receiving the arthritogenic composition to be tested, administered either before, together, or after the arthritogenic serum or immunoglobulins; ii) detecting the time course of inflammation and joint destruction in said first mouse; and iii) comparing the time course of inflammation and joint destruction in said first mouse to the time course of inflamation and joint destruction in a second mouse of same genotype receiving the same arthritogenic serum or immunoglobulins but which has not been exposed to said anti-arthritic composition.

Another possibility for step ii) is to detect the extent of inflammation, joint destruction and limb deformation in said first mouse; and for step iii) to compare the extent of inflammation, joint destruction and limb deformation in said first mouse to the extent of inflammation, joint destruction and limb deformation in a second mouse of same genotype receiving the same arthritogenic serum or immunoglobulins but which has not been exposed to said anti-arthritic composition.

In this process, the arthritogenic immunoglobulins can be monoclonal antibodies or combinations thereof, especially antibodies described below.

It is also possible to test molecules which are able to modulate the production of GPI or GPI like proteins in order to treat arthritis, said molecule may be for example antibodies which are non pathogenic.

It is also possible to use surface coated with GPI or GPI like proteins for treatment of serum in an extracorporeal circuit for depleting the quantities of pathological antibodies.

Another aspect of the invention relates to a process for isolating monoclonal antibodies capable of transferring arthritis comprising the steps consisting of:
a) preparing hybridomas from lymphocytes of arthritic mammals splenocytes, preferably from K/BxN mice splenocytes,
b) selecting said hybridomas in limited dilution conditions in HAT medium,
c) screening hybridomas producing antibodies directed against GPI or GPI like proteins in an ELISA assay,
d) expansion and cloning of the selected hybridromas at step c),
e) testing said antibodies produced by selected hybridomas at step d) in combination or alone for their ability to transfer arthritis.

The testing of step e) can be achieved by i): administering a known dose of said antibodies to a normal mouse; ii) detecting the onset of inflammation joint destruction and limb deformation in said mouse.

It is to be understood that the above process steps can be achieved with well known techniques pertaining to the art and are not limited to any particular procedure.

So, the invention is directed to monoclonal antibodies obtainable by such a process and to hybridoma lines producing said antibodies. Among the antibodies depicted at example 5, antibodies 2.99 and 6.121 are preferred (see FIG. 9 below). These antibodies can be used to the same ends as the serum or anti-GPI immunoglobulins described above.

Some additional characteristics and advantages of this invention will appear from the following examples which will be explain in reference to the figures wherein:

FIG. 1. Serum from K/BxN mice can transfer arthritis.

A: Paws of normal mice injected 72 h previously with 150 µl of serum from an arthritic K/BxN mouse, or from a control (ctl) non-arthritic littermate. Note the swelling and redness in the mouse injected with arthritic serum. Arthritis can be objectivated by measurement of ankle thickness or clinical index assessement (right panels); the clinical score is defined as: 0, normal; 1, doubt; 2, two paws affected; 3, three paws affected; 4, all limbs affected.

B: Disease induced by serum transfer is present in all recipients, whether transgenic or not, but is more intense in recipients which possess autoreactive T cells but cannot develop arthritis for lack of B cells (K/BxN-μM$^{o/o}$).

C: Wane of arthritis, read out as clinical index, after a short course of K/BxN serum administration (open dots), but persistence after repeated injection (black dots).

D: Arthritogenic activity of the serum IgG fraction. Left panel: RAG$^{o/o}$ mice were injected with similar amounts (relative to starting volumes) of serum from arthritic K/BxN mice (stars), the flow-through (crosses) or the fraction eluted from a protein-G column (closed circles). Right panel: twice the amount of IgG from non-TCR tg littermates was incapable of inducing arthritis.

FIG. 2. Serum from K/BxN mice can transfer arthritis.

Knee sections from a typical K/BxN mouse (left) or a normal mouse 10 days after two injections of 200 μl serum from an arthritic K/BxN animal (right). Note in both cases the thickened synovial lining, the massive underlying inflammatory infiltration, which extends over the cartilage and begins its destruction, and the presence of polymorphonuclear cells in the articular cavity. Hematoxylin and eosin (H+E) staining, 10× objective.

Figure 3:
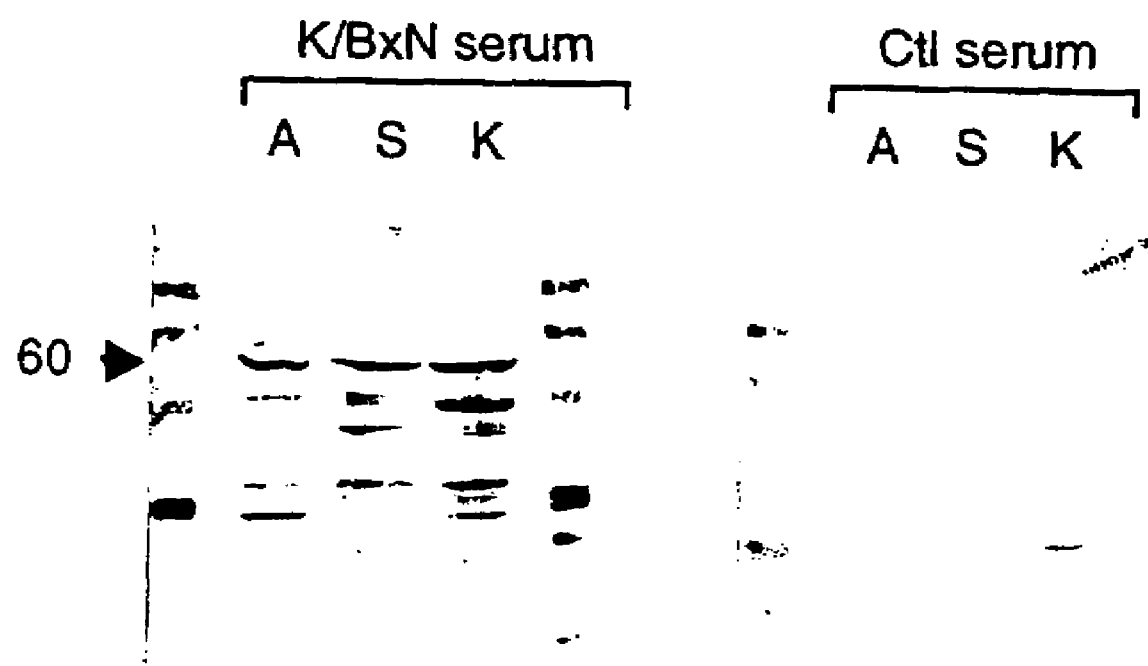

FIG. 3. A 60 kD protein is the major target of K/BxN autoantibodies.

Total protein extracts (NP-40 extraction) from ankle (A), spleen (S) or kidney (K) were run on SDS-PAGE, transferred by electroblotting, and probed with serum from a K/BxN arthritic mouse or a control littermate. The position of the prominent 60 kD band is indicated FIG. 4. The 60 kD protein target of K/BxN serum is glucose-6-phosphate isomerase.

The 60 kD protein SEQ ID NO 1 from kidney extracts was immunopurified on immunadsorbents made with K/BxN immunoglobulins. After digestion with trypsin, peptides were purified by HPLC, and several sequenced by automated Edman degredation. The three peptide sequences obtained belong to glucose-6-phosphate isomerase, and are underlined. Further confirming this identification, the molecular weight of a fourth peptide was determined by mass spectrometry, and concides perfectly with the mass of a tryptic fragment of GPI (wavy underline).

Figure 5:
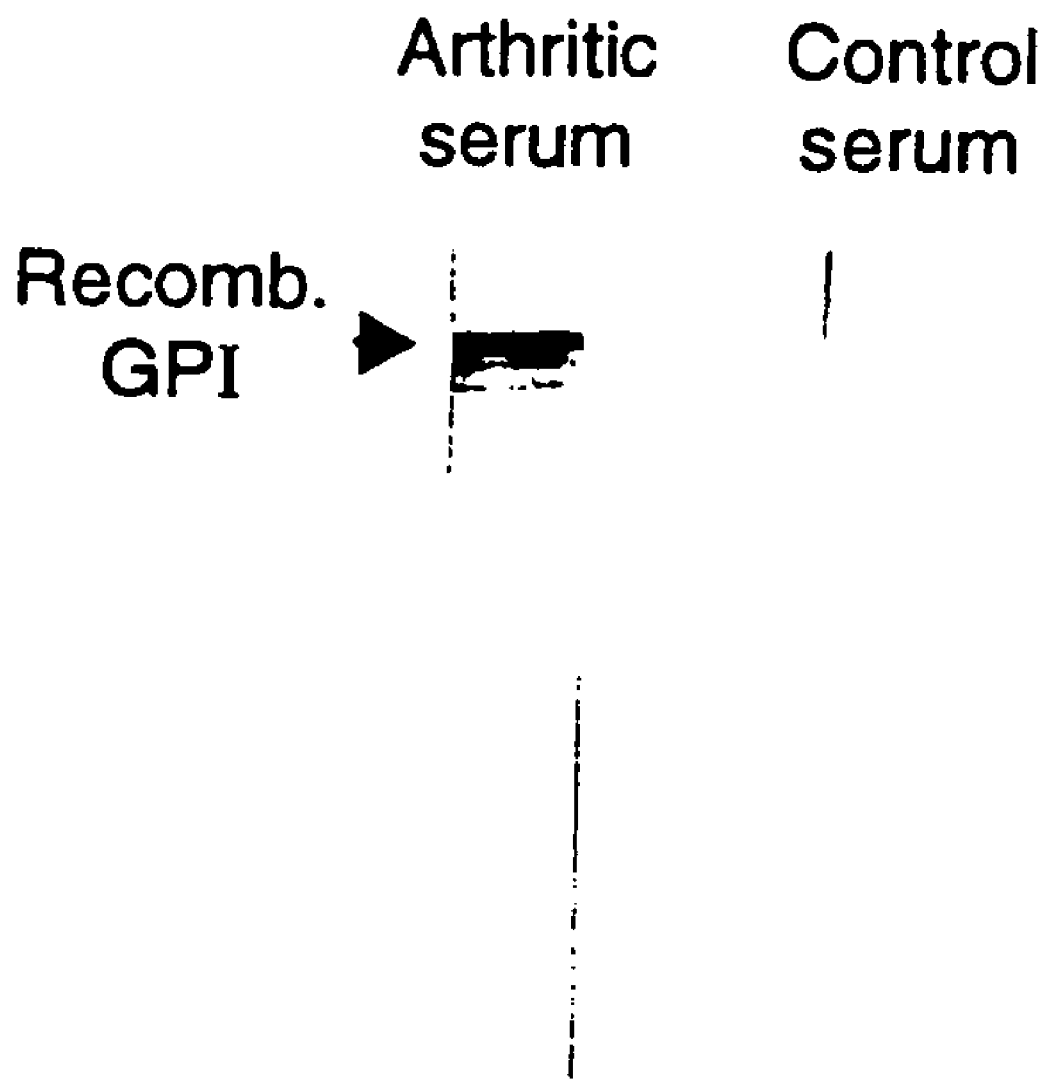

FIG. 5. Arthritic serum binds recombinant GPI.

A western blot was performed as in FIG. 3, except that the protein loaded was recombinant GPI produced in *E. Coli* (as a fusion protein with GST). The blots were probed with serum from an arthritic K/BxN or a control mouse.

Figure 6:
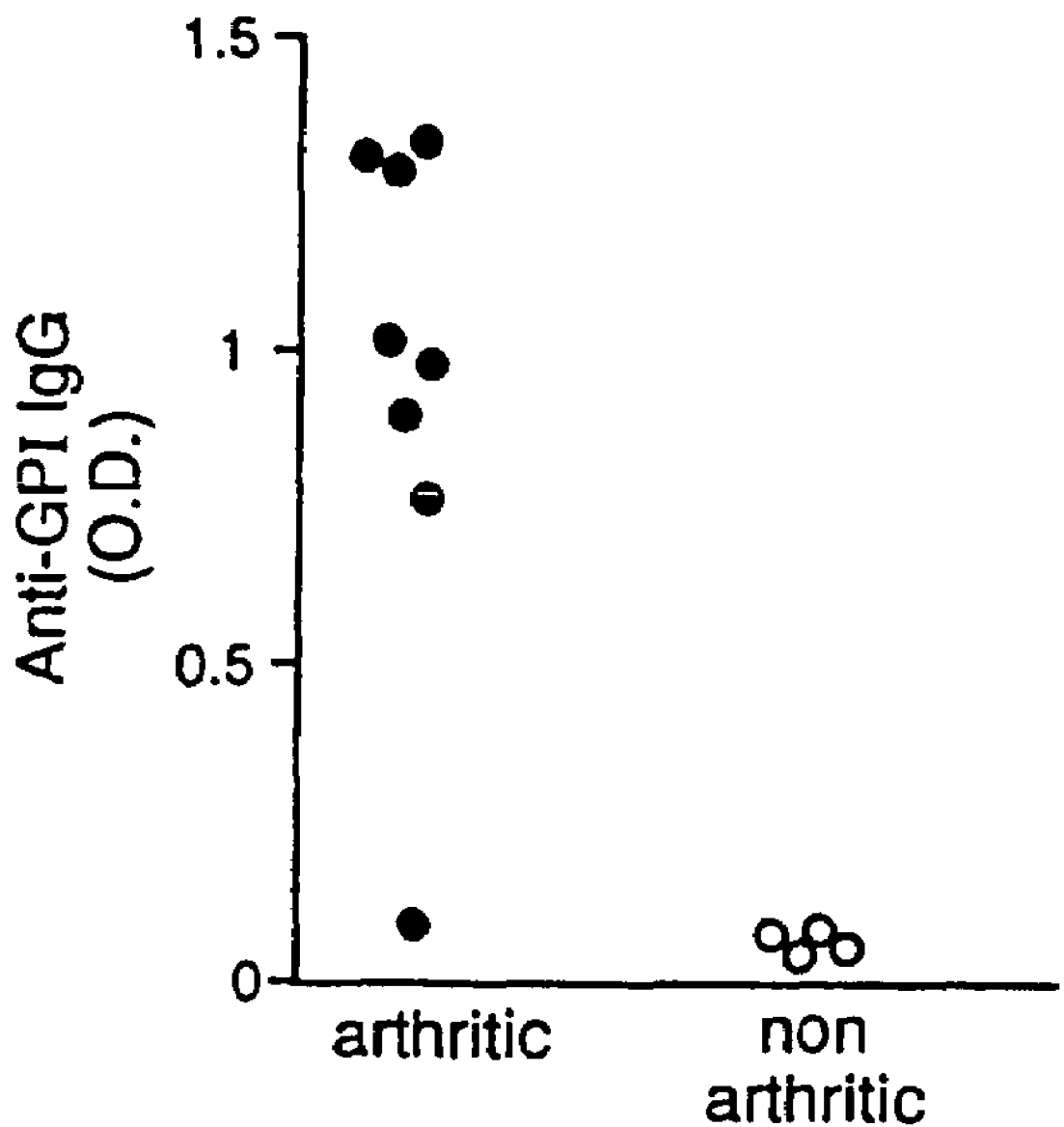

FIG. 6. ELISA assay detects anti-GPI antibodies in sera from arthritic mice, but not in controls.

In this enzyme-linked immunoassay, recombinant GPI, produced as above, was used to coat wells of ELISA plates. These were used to test for anti-GPI IgG in sera from arthritic or control mice. The values shown here were obtained with serum dilutions of 1/16000, but positive signals could still be obtained with dilutions as great as 1/1,000,000. The only negative arthritic mouse in the assay was an animal that had become arthritic on the very day the serum was taken.

Figure 7A:
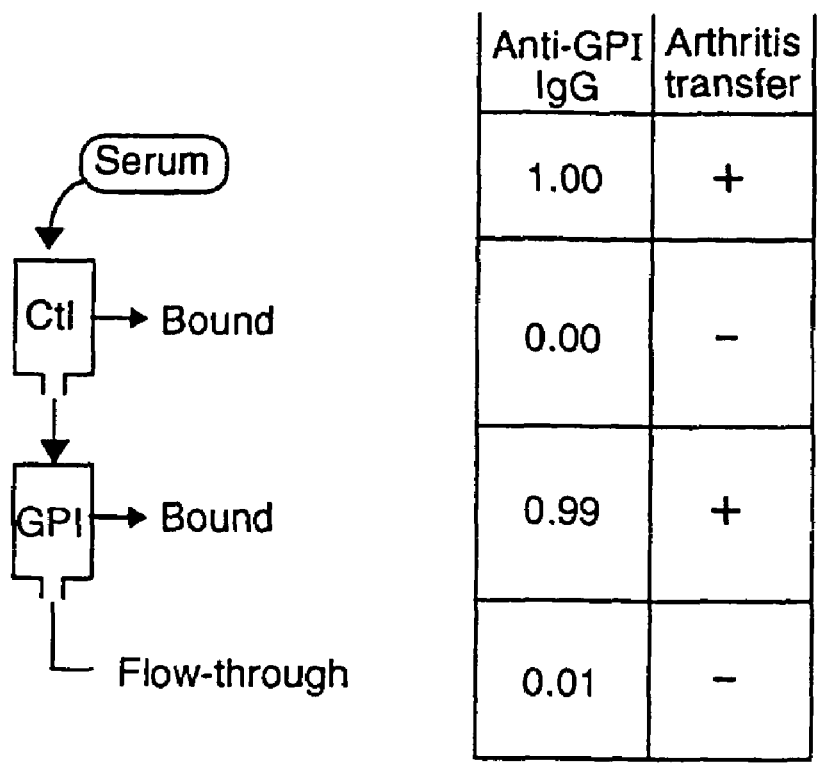
Figure 7B:
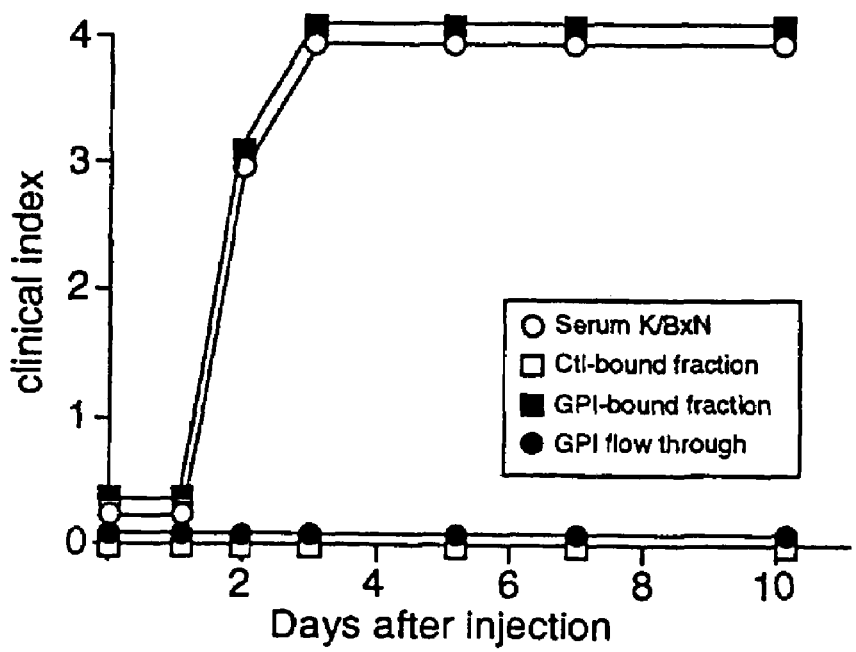

FIG. 7. Serum from K/BxN mice can transfer arthritis.

A: Recombinant GPI, or control recombinant protein—GST alone—, produced as above, was bound to a solid support, and used as an immunoadsorbent to remove anti-GPI antibodies from K/BxN serum. All the anti-GPI IgG was in the bound fraction, as expected. The ability to transfer arthritis was only found in the bound fraction, and eliminated from the fraction which flowed through the column.

B: A representative experiment, in which normal mice were injected with various fractions from the purification scheme shown in A. Arthritis was evaluated and scored as above.

Figure 8:
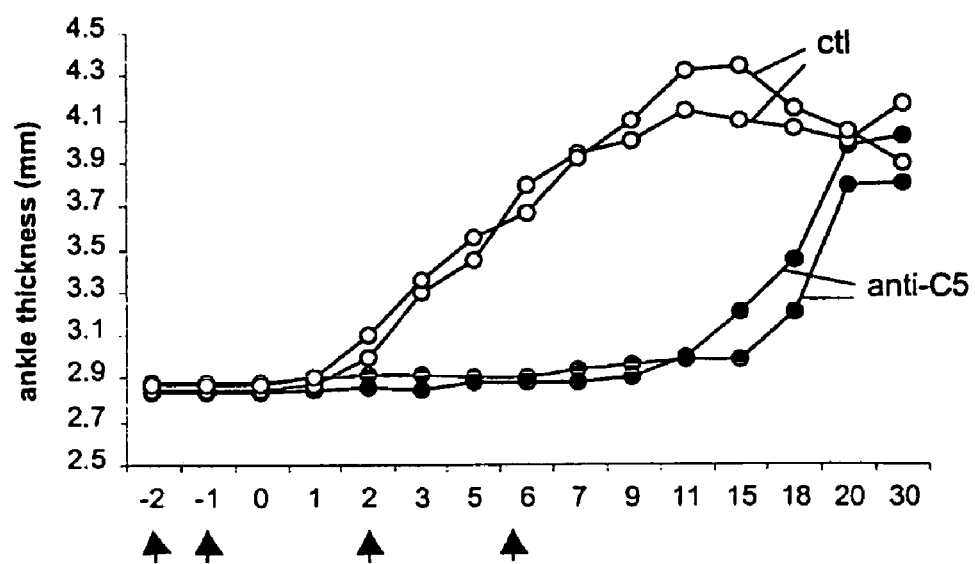

FIG. 8. Transfert of K/BxN serum can test therapeutic potential of a monoclonal antibody treatment.

Naïve 4 week old mice of the C57B1/6 strain were injected with 200 μl of pooled serum from K/BxN mice on days 0 and 3. The mice were also injected with test antibody BB5.1, which blocks the C5 complement factor, at days −2, −1, +1, +5, and +8, or with vehicle only. The onset of arthritis was followed by measuring ankles thickness in the following days. Mice treated with monoclonal antibody were protected from arthritis, while those injected with vehicle only presented disease.

Figure 9:
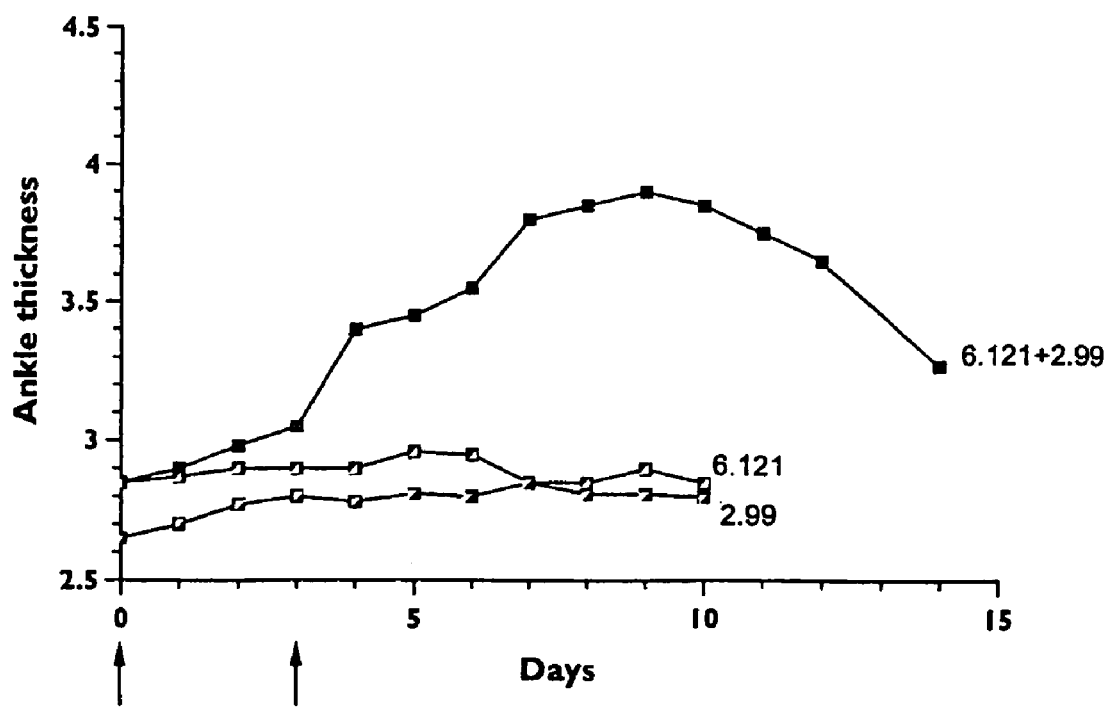

FIG. 9. Monoclonal anti-GPI antibodies induce arthritis when injected together in naïve mice.

Naïve 4 week old mice of the Balb/c strain were injected with 1 mg of purified IgG from anti-GPI mAbs 6.121 and 2.99 dissolved in Phosphate-buffered Saline, or 1 mg of each, on days 0 and 3, the onset of arthritis was followed by measuring ankle thickness in the following days. Mice treated with the two anti-GPI monoclonal antibodies in combination showed arthritis, but not those injected with either mAb alone.

EXAMPLE 1

Immunoglobulins Mediate KRN Arthritis

Figure 1B:
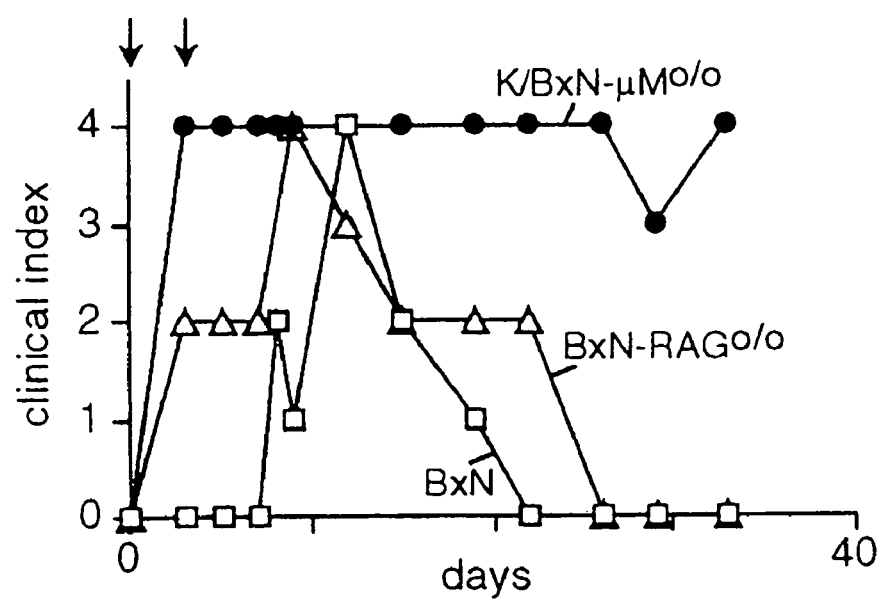

We have previously shown ((Kouskoff et al., 1996), U.S. Pat. No. 5,675,060) that mice carrying all the genetic elements needed for the appearance of KRN arthritis, but deficient in B lymphocytes, are free of disease. To explore the possibility that arthritis development in the KRN model depends critically on a particular B cell product, we tried to provoke disease in non-arthritic mice by transfer of serum from K/BxN mice. Severe joint swelling appeared in the animals injected with serum from arthritic K/BxN donors, but not in those receiving serum from non-arthritic BxN controls (FIG. 1A). Disease could be induced with as little as 100 μl of K/BxN serum, and showed up reproducibly. It was provoked very rapidly, measured by either clinical score or ankle thickness, evident already within two days after serum injection. Arthritis could be obtained upon injecting sera from arthritic donors into normal mice, lymphocyte-deficient RAG$^{o/o}$ hosts, or B cell deficient K/BxN mice (K/BxN mice-μMT$^{o/o}$) (FIG. 1B). These results show that serum components from K/BxN mice are sufficient to confer arthritis, although the more agressive disease seen with the latter animals indicates that K/BxN T cells probably play an accessory enhancing role in the effector phase.

The arthritis provoked by serum transfer presents all of the histological features of the disease in regular K/BxN mice, including invasion of inflammatory cells, hyperplasia of synoviocytes, pannus formation, and cartilage destruction (FIGS. 2A and B).

Figure 1C:
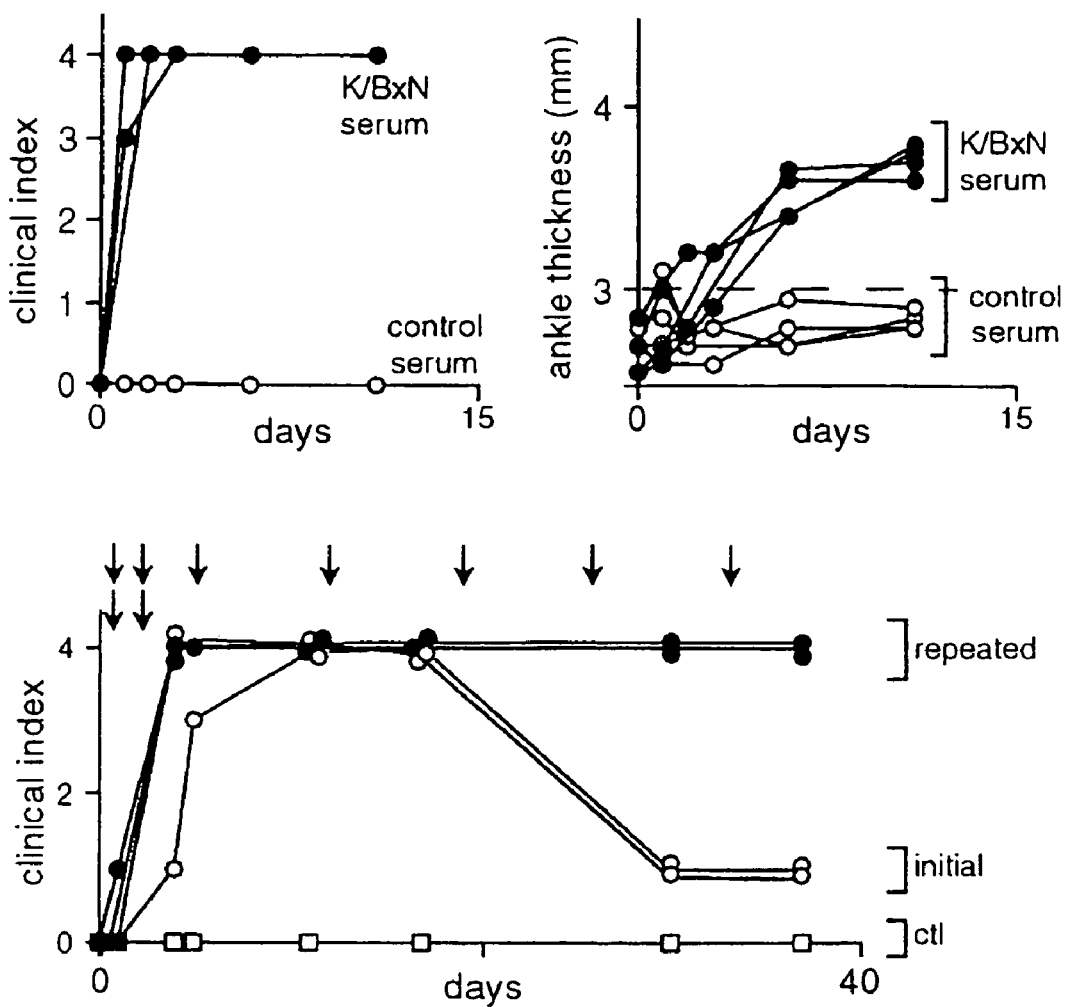
Figure 1D:
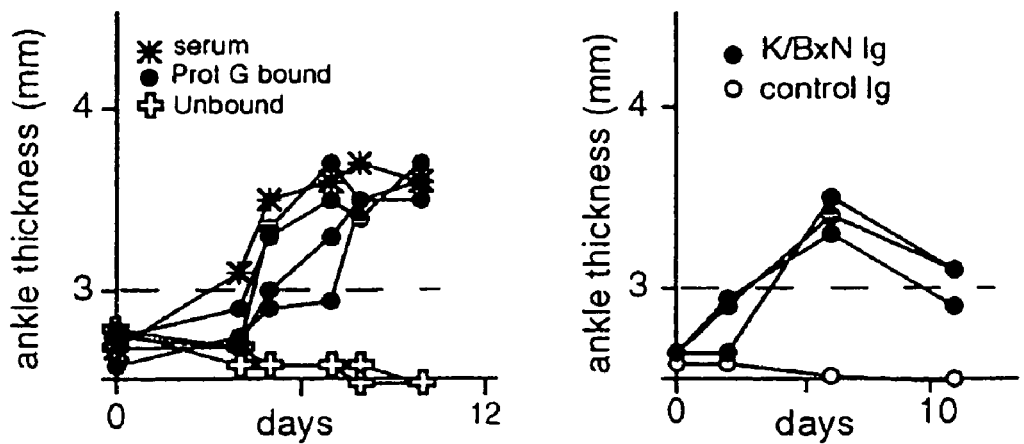

The arthritis induced by serum injection is transient. In mice that had received a single pair of injections, joint inflammation began to subside after about 15 days (FIG. 1C); after 30 days, some of the joints appeared quite normal, even in the animals that had initially been fully arthritic. Disease transience could be overcome by repeated injections of serum from arthritic mice (FIG. 1C). That this was true even for RAG$^{o/o}$ recipients suggests that instability of the serum compound is the explanation for the transient nature of the disease.

The arthritogenic serum factor is a B cell-produced immunoglobulin (Ig): after fractionation of serum from K/BxN mice into IgG and non-IgG components, only the IgG fraction is capable of provoking arthritis in RAG$^{o/o}$ hosts; its potency is similar to that of whole serum (relative to the starting volume) (FIG. 1D), as are the histological features of the disease it induced (data not shown).

EXAMPLE 2

Molecular Target of the Pathogenic Immunoglobulins

Thus, an Ig produced by B lymphocytes is key to arthritis development in K/BxN mice. We then attempted to define their molecular targets. At the onset, one could have imagined that these could be antibodies directed against specific components of the joint, somehow generated by the interaction of transgenic T cells reactive against the Ag7 molecule on the surface of B cells; this could prevent the normal tolerance of B cells towards self-components, or induce polyclonal B cell stimulation and the synthesis of Ig reactive against self (perhaps polymeric) components. We addressed this question:

1) By immunohistochemical analysis of RAGo/o mice after transfer of Ig from K/BxN mice. These analyses showed deposition of transferred Ig not only in the synovial tissue of the joint, but also in lining membranes of many other organs (spleen, kidney, liver, muscle; data not shown).

2) By Western blot analysis: Whole protein extracts were prepared from the ankle joint and from several other organs of RAG$^{o/o}$ mice (to avoid the presence of Ig in the extract), electrophoresed on denaturing poyacrylamide gels (SDS-PAGE), blotted, and probed with serum from K/BxN mice. Ig binding was revealed by probing with HRP-conjugated anti-mouse IgG. As can be seen on FIG. 3, a single dominant protein band could be detected on these blots, at approximately 60 kD MW. This band was seen repeatedly when sera from a number of K/BxN arthritic mice were used, but not with sera from control non arthritic littermates. Other proteins were detected with some of the sera, but inconsistently and they were always weaker than the 60 kD band.

We then attempted to identify this 60 kD protein. To this end, IgG from a large pool of K/BxN sera was purified by affinity chromatography on ProteinG columns. This purified Ig (1.5 mg) was covalently bound to CNBr-activated Sepharose. This matrix was then used as an immunoadsorbant on which were loaded 50 mg of NP-40 extract from kidney of RAG$^{o/o}$ mice. The column was washed extensively, and bound proteins eluted at acid pH. They were analyzed by SDS-PAGE and Coomassie staining. As expected from the results described above, a dominant band of 60 kD was seen. This band was excised, the protein digested in the gel slice by Trypsin, as described in (Rosenfeld et al., 1992), and the resulting peptides resolved by reverse-phase HPLC. Several peptides were identified. Three of them were then sequenced by automated Edman degradation on an Applied Biosystems 470A instrument. The sequences were compared to public databases, using the BLAST program on the Swissprot database. All three were found to belong to the protein glucose-6-phosphate isomerase (aka phosphohexose-isomerase; EC 5.3.1.9; Swissprot database number P06745; sequence accession # 1230741; hereafter abbreviated as GPI). Their positions are shown in FIG. 4. Another of the peptides obtained was also found to belong to GPI, on the basis of mass spectrometry analysis which fit exactly with the molecular weight predicted from the sequence (FIG. 4).

The molecular weight of GPI (62 636 kD) is very concordant with the MW of the target of K/BxN serum predicted from the Western blots, within the precision of MW estimation by PAGE.

GPI is an essential enzyme of the glycolytic pathway. It is an enzyme expressed in essentially all tissues, whether normal or tumoral, with some quantative variations, from the earliest stages of embryogenesis to late in life of the animals (West et al., 1990; Hallbook et al., 1989; Warner et al., 1985). It is normally a cytoplasmic enzyme, but soluble GPI can be found in serum; it is found elevated in tumor patients (various organs), but not in a manner that make it a reliable marker (see for example (Neri et al., 1983; Schwemmer et al., 1985; Paulick et al., 1987; Gomm et al., 1988; Gurney et al., 1986)). GPI has also been purified independently as "Neuroleukin", "Maturation factor", or "Autocrine Motility Factor", secreted factors of often limited potency as a neurotrophic agent, or as agents promoting cell migration or tumor cell differentiation (Gurney et al., 1986; Faik et al., 1988; Niinaka et al., 1998; Xu et al., 1996). Genetic deficiencies in GPI result in hemolytic anemia syndromes (see for example (Kanno et al., 1996; Baronciani et al., 1996)).

To confirm that GPI is the protein recognized by the Igs present in K/BxN serum, we produced recombinant GPI in *E. Coli*. The coding sequence of mouse GPI was amplified by Polymerase Chain Reaction, and the product cloned in the plasmid pGEx-4T-3 (Pharmacia). The recombinant protein, a fusion product with Glutathione-S-transferase, was purified by affinity chromatography on Glutathione-Sepharose 4B column. The product was characterized on SDS-PAGE, and showed the expected size (data not shown). The gel was blotted, and strips were probed with sera from K/BxN or non-transgenic littermate controls. As can be seen in FIG. 5, all K/BxN sera reacted strongly, while control sera were negative, confirming that the GPI protein is the molecular target of anti-60 kD antibodies in K/BxN serum.

The recombinant protein was also used in Enzyme Linked ImmunoSorbent Assays (ELISA) to detect reactivity to GPI in sera of K/BxN mice of different ages. As previously described (Kouskoff et al., 1996), KRN arthritis appears at 28-32 days of age. As shown in FIG. 6, the assay detected significant reactivity above background, up to dilutions of 1/20 000, in sera from K/BxN mice. No such reactivity was seen in control littermates. The assay can thus serve as a good diagnostic test of arthritis in these mice.

EXAMPLE 3

Anti-GPI Antibodies are the Pathogenic Immunoglobulins

Do anti-GPI antibodies constitute all the pathogenic specificities of K/BxN serum, and can their removal eliminate the pathogenic potential of the serum. To address this question, we coupled 5 mg of recombinant GPI or of control GST protein, prepared as above, to CNBr-conjugated Sepharose. Pooled sera from K/BxN mice were applied sequentially to these columns. The bound proteins were eluted at acid pH, and tested by transfer into naive mice, along with an aliquot of the starting material and of flow-through fractions. As shown in FIG. 7, all arthritogenic activity was found in the fraction bound to the GPI-conjugated column, and none in the flow-through, even though the latter contained the majority of the immunoglobulin. These results demonstrate that anti-GPI antibodies are indeed the pathogenic Ig in serum from arthritic K/BxN mice, and that it can be adsorbed with recombinant GPI protein.

From these data, we conclude that anti-GPI antibodies produced in the transgenic mice provoke arthritis. We have found (unpublished data) that T cells expressing the KRN receptor are specifically stimulated by antigen-presenting-cells exposed to GPI antigen. These T cells in turn stimulate B cells producing anti-GPI immunoglobulin, which internalize GPI effectively and thus receive help from T cells more readily than non-specific B cells (Lanzavecchia, 1985). It is thus proposed that self-reactive T cells against GPI or related circulating proteins, present in limited amounts in the circulation and thus unable to induce a paralyzing tolerance of the immune system, could induce similar arthritogenic antibodies in human conditions such as RA.

EXAMPLE 4

The transfer of serum from arthritic K/BxN offers a model wherein potential anti-arthritic formulations can be tested by administration concomitant with the arthritogenic serum or immunoglobulins.

As a proof of principle, we tested the ability of anti-C5 monoclonal antibody to interfere with arthritogenesis on the K/BxN model. We chose this reagent because of prior evidence implicating complement components, and in particular C5, in the generation of joint lesions in other mouse models of arthritis and in human RA patients (Watson et al, 1987; Wang et al, 1995). Mice were injected with arthritogenic serum from K/BxN mice, and at the same time with the anti-C5 monoclonal antibody BB5.1, known to block C5 activity (Frei et al, 1987). As can be seen from FIG. 8, mice injected with the anti-C5 monoclonal were protected from disease.

EXAMPLE 5

If immunoglobulins present in the serum of K/BxN mice are able to transfer arthritis, it should be possible to isolate monoclonal antibodies (mAbs) also able to transfer disease to naïve recipients. Splenocytes from 30 and 50 days old K/BxN mice were fused according to standard protocols for hybridoma derivation (de St Groth and Scheidegger, 1980), and hybridomas selected in HAT medium in limiting dilution conditions in 96-well plates. Hybrids were screened for production of immunoglobulins reactive to GPI by testing culture supernatants in an ELISA assay with recombinant GPI as a bound antigen and anti-mouse IgG as a developing reagent. Several positive wells were selected for expansion, cloning by limiting dilution and testing for stability of the hybridoma lines. Eleven stable hybridoma lines producing anti-GPI IgG were thus obtained (see Table 1 below).

TABLE 1

Anti-GPI monoclonal antibodies

| Monoclonal Antibody | Recognized Peptide | Isotype |
| --- | --- | --- |
| 1.8 | 277-312 | IgG1, κ |
| 1.7 | 1-36 | IgG1 |
| 1.11 | 47-82 | IgG1 |
| 1.24 | 24-59 | IgG1, κ |
| 2.99 | conf. | IgG1, κ |
| 2.56 | 300-335 | IgG2b, κ |
| 2.67 | 277-312 | IgG2b, κ |
| 6.149 | 277-312 | IgG1, κ |
| 6.121 | 277-312 | IgG1, κ |
| 6.65 | conf. | IgG1, λ |
| 6.96 | 277-312 | IgG1, κ |

The ability of these monoclonals to transfer disease was tested by Protein-G purification of mg amounts of the IgG produced by these hybridomas, and intravenous injection into naïve Balb/c recipients. As can be seen on FIG. 9, the coupled injection of anti-GPI immunoglobulin from the 6.121 and 2.99 hybridoma cells provoked arthritis in the recipients, but none of the antibodies were able to induce disease when injected alone. Among these antibodies, some works, such as the 2.99 and 6.121 antibodies, while others don't. However, step e) of the process for isolating antibodies capable of transferring arthritis according to the invention allows to select the working ones.

REFERENCES

Baronciani, L., Zanella, A., Bianchi, P., et al. (1996). Study of the molecular defects in glucose phosphate isomerase-deficient patients affected by chronic hemolytic anemia. Blood. 88, 2306-2310.

Claque, R. B. and Moore, L. J. (1984). IgG and IgM antibody to native type II collagen in rheumatoid arthritis serum and synovial fluid. Evidence for the presence of collagen-anticollagen immune complexes in synovial fluid. Arthritis Rheum. 27, 1370-1377.

De St Groth, S. F. and Scheidegger D., 1980. Production of monoclonal antibodies: strategy and tactics. J. Immunol. Meth. 35:1

Faik, P., Walker, J. I., Redmill, A. A., and Morgan, M. J. (1988). Mouse glucose-6-phosphate isomerase and neuroleukin have identical 3' sequences. Nature 332, 455-457.

Feldmann, M., Brennan, F. M., and Ravider, N. M. (1996). Rheumatoid Arthritis. Cell 85, 307-310.

Frei, Y., Lambris, J. and Stockinger, B. 1987. Generation of a monoclonal antibody to mouse C5. Mol. Cell. Probes, 1:141-9

Gomm, S. A., Keevil, B. G., Thatcher, N., Hasleton, P. S., and Swindell, R. S. (1988). The value of tumour markers in lung cancer. Br. J. Cancer 58, 797-804.

Gurney, M. E., Heinrich, S. P., Lee, M. R., and Yin, H. S. (1986). Molecular cloning and expression of neuroleukin, a neurotrophic factor for spinal and sensory neurons. Science 234, 566-574.

Hallbook, F., Persson, H., Barbany, G., and Ebendal, T. (1989). Development and regional expression of chicken neuroleukin (glucose-6-phosphate isomerase) messenger RNA. J. Neurosci. Res. 23, 142-151.

Kanno, H., Fujii, H., Hirono, A., et al. (1996). Molecular analysis of glucose phosphate isomerase deficiency associated with hereditary hemolytic anemia. Blood. 88, 2321-2325.

Korganow A S, Ji H, Mangialaio S, Duchatelle V, Pelanda R, Martin T, Degott C, Kikutani H, Rajewsky K, Pasquali J L, Benoist C, Mathis D (1999). From systemic T cell self-reactivity to organ-specific autoimmune disease via immunoglobulins. Immunity. April; 10(4):451-61.

Kouskoff, V., Korganow, A-S., Duchatelle, V., Degott, C., Benoist, C., and Mathis, D. (1996). Organ-specific disease provoked by systemic autoreactivity. Cell 87, 811-822.

Lanzavecchia, A. (1985). Antigen-specific interaction between T and B cells. Nature 314, 537-539.

Mannik, M. (1992). Rheumatoid factors in the pathogenesis of rheumatoid arthritis. J. Rheumatol. Suppl. 32, 46-49.

Matsumoto I, Staub A, Benoist C, Mathis D. (1999). Arthritis provoked by linked T and B cell recognition of a glycolytic enzyme. Science. Nov. 26; 286(5445):1732-5.

Neri, B., Becucci, A., Ciapini, A., Comparini, T., Guidi. G., and Guidi, S. (1983). Chronobiological aspects of phosphohexoseisomerase in monitoring multiple myeloma. Oncology. 40, 332-335.

Niinaka, Y., Paku, S. Haga, A., Watanabe, H., and Raz, A. (1998). Expression and secretion of neuroleukin/phosphohexose isomerase/maturation factor as autocrine motility factor by tumor cells. Cancer Res. 58, 2667-2674.

Panayi, G. S., Lanchbury, J. S., and Kingsley, G. H. (1992). The importance of the T cell in initiating and maintaining the chronic synovitis of rheumatoid arthritis. Arthritis Rheum. 35, 729-735.

Paulick, R., Caffier, H., and Paulick, M. (1987). Comparison of serum CEA, PHI, and TPA as tumor markers in breast cancer patients. Cancer Detect. Prev. 10, 197-203.

Rosenfeld, J., Capdevielle, J., Guillemot, J-C., and Ferrara, P. (1992). In-gel digestion of proteins for internal sequence analysis after one- or two-dimensional gel electrophoresis. Analytical Biochemistry 203, 173-179.

Rudolphi, U., Rzepka, R., Batsford, S., et al. (1997). The B cell repertoire of patients with rheumatoid arthritis. II. Increased frequencies of IgG+ and IgA+ B cells specific for mycobacterial heat-shock protein 60 or human type II collagen in synovial fluid and tissue. Arthritis Rheum. 40, 1409-1419.

Schwemmer, B., Schutz, W., Kuntz, R. M., and Lehmer, A. (1985). Simultaneous determination of six tumor markers in patients with prostatic carcinoma and bladder tumors. Urol. Res. 13, 133-136.

Sebbag, M., Simon, M., Vincent, C., et al. (1995). The anti-perinuclear factor and the so-called anti-keratin antibodies are the same rheumatoid arthritis-specific autoantibodies. J. Clin. Invest. 95, 2672-2679.

Thomas, R. and Lipsky, P. E. (1996). Presentation of self peptides by dendritic cells: possible implications for the pathogenesis of rheumatoid arthritis. Arthritis Rheum. 39, 183-190.

Wang Y, Rollins S A, Madri J A, Matis L A. 1995. Anti-C5 monoclonal antibody therapy prevents collagen-induced arthritis and ameliorates established disease. Proc Natl Acad Sci USA. 92:8955-9.

Warner, C. M., Briggs, C. J., Balinsky, D., and Meyer, T. E. (1985). Glucose phosphate isomerase activity in C57BL/6 and a mice of different ages. Gerontology. 31, 315-320.

Watson W C, Brown P S, Pitcock J A, Townes A S. 1987. Passive transfer studies with type II collagen antibody in B10.D2/old and new line and C57B1/6 normal and beige strains: evidence of important roles for C5 and multiple inflammatory cell types in the development of erosive arthritis Rheum. 30:460-5.

West, J. D., Flockhart, J. H., Peters, J., and Ball, S. T. (1990). Death of mouse embryos that lack a functional gene for glucose phosphate isomerase. Genet Res. 56, 223-236.

Xu, W., Seiter, K., Feldman, E., Ahmed, T., and Chiao, J. W. (1996). The differentiation and maturation mediator for human myeloid leukemia cells shares homology with neuroleukin or phosphoglucose isomerase. Blood. 87, 4502-4506.

Zvaifler, N. J. (1973). The immunopathology of joint inflammation in rheumatoid arthritis. Adv. Immunol. 265, 265-336.

---

The invention claimed is:
1. A method comprising injecting arthritic K/BxN transgenic mouse serum into a mouse, wherein the injected mouse develops arthritis.

* * * * *